(12) United States Patent
Herring et al.

(10) Patent No.: US 8,765,428 B2
(45) Date of Patent: Jul. 1, 2014

(54) FLOW-THROUGH BIOLOGICAL CONVERSION OF LIGNOCELLULOSIC BIOMASS

(75) Inventors: Christopher D. Herring, Lebanon, NH (US); Chaogang Liu, Hanover, NH (US); John Bardsley, Newport, NH (US)

(73) Assignee: Mascoma Corporation, Waltham, MA (US)

( * ) Notice: Subject to any disclaimer, the term of this patent is extended or adjusted under 35 U.S.C. 154(b) by 299 days.

(21) Appl. No.: 13/054,750

(22) PCT Filed: Jul. 17, 2009

(86) PCT No.: PCT/US2009/004135
§ 371 (c)(1),
(2), (4) Date: Apr. 14, 2011

(87) PCT Pub. No.: WO2010/008578
PCT Pub. Date: Jan. 21, 2010

(65) Prior Publication Data
US 2012/0028325 A1 Feb. 2, 2012

Related U.S. Application Data

(60) Provisional application No. 61/081,966, filed on Jul. 18, 2008.

(51) Int. Cl.
*C12P 7/10* (2006.01)
*C12P 1/00* (2006.01)
*C12P 7/36* (2006.01)
*C12P 7/06* (2006.01)

(52) U.S. Cl.
USPC .............. 435/165; 435/41; 435/151; 435/161

(58) Field of Classification Search
None
See application file for complete search history.

(56) References Cited

U.S. PATENT DOCUMENTS

| | | | |
|---|---|---|---|
| 1,882,391 A | | 10/1932 | Morterud |
| 4,511,433 A | * | 4/1985 | Tournier et al. .................. 162/16 |
| 5,705,369 A | * | 1/1998 | Torget et al. ................... 435/105 |
| 2004/0185542 A1 | * | 9/2004 | Yang et al. ..................... 435/161 |
| 2006/0088922 A1 | | 4/2006 | Yang et al. |

FOREIGN PATENT DOCUMENTS

| | | |
|---|---|---|
| GB | 720004 | 12/1954 |
| WO | WO 2004/081207 | 9/2004 |
| WO | WO 2008/155636 | 12/2008 |
| WO | WO 2009/058276 | 5/2009 |

OTHER PUBLICATIONS

Tan, et al., "Column cellulose hydrolysis reactor: An efficient cellulose hydrosis reactor with continuous cellulase recycling," *Applied Microbiology and Biotechnology* 25:250-55, Springer Verlag, Berlin, DE (1986).
Isaacs, S. H., "Ethanol Production by Enzymatic Hydrolysis," *U.S. Dept. of Energy*, Solar Energy Research Institute, Golden, CO (1984) available, at http://nrel.gov/docs/legosti/old/2093.pdf, retrieved on Jan. 19, 2009.
Tu, et al., "Recycling cellulases during the hydrolysis of steam exploded and ethanol pretreated lodgepole pine," *Biotechnology Progress* 23:1130-137, American Chemical Society and American Institute of Chemical Engineers (2007).

* cited by examiner

*Primary Examiner* — Chris R Tate
*Assistant Examiner* — Douglas F White
(74) *Attorney, Agent, or Firm* — Sterne, Kessler, Goldstein & Fox P.L.L.C.

(57) ABSTRACT

The present invention is directed to a process for biologically converting carbohydrates from lignocellulosic biomass comprising the steps of: suspending lignocellulosic biomass in a flow-through reactor, passing a reaction solution into the reactor, wherein the solution is absorbed into the biomass substrate and at least a portion of the solution migrates through said biomass substrate to a liquid reservoir, recirculating the reaction solution in the liquid reservoir at least once to be absorbed into and migrate through the biomass substrate again. The biological converting of the may involve hydrolyzing cellulose, hemicellulose, or a combination thereof to form oligosaccharides, monomelic sugars, or a combination thereof; fermenting oligosaccharides, monomelic sugars, or a combination thereof to produce ethanol, or a combination thereof. The process can further comprise removing the reaction solution and processing the solution to separate the ethanol produced from non-fermented solids.

27 Claims, 2 Drawing Sheets

FLOW-THROUGH BIOLOGICAL CONVERSION OF LIGNOCELLULOSIC BIOMASS

FEDERALLY SPONSORED RESEARCH AND DEVELOPMENT

This invention was funded, in part, by the United States government under a grant with the Department of Energy, Award # DE-FC36-07GO17057. The U.S. government has certain rights in this invention.

BACKGROUND OF THE INVENTION

1. Field of the Invention

The present invention is directed to processes for biologically converting lignocellulosic biomass. Particularly, the invention relates to an improved method to ferment biomass material, which reduces the need for costly physical agitation, for the production of ethanol. Additionally, other useful chemical products can be produced from the biological conversion of the biomass.

2. Background Art

Lignocellulosic biomass, which is available in abundance, can be used as a feedstock for production of fuels and chemical. A variety of plant biomass resources are available as lignocellulosic materials for the production of biofuels, notably bioethanol. The major sources are (i) wood residues from paper mills, sawmills and furniture manufacturing, (ii) municipal solid wastes, (iii) agricultural residues and (iv) wood chips, and (v) energy crops.

Independent of the status and future prospects of the corn ethanol industry, ethanol production from cellulosic biomass, such as wood, grass, and agricultural residues, has attracted a great deal of attention of late. Although cellulosic ethanol is not yet produced commercially, projected features include a decisively positive fossil fuel displacement ratio, near-zero net greenhouse gas emissions, potential for substantial soil fertility and carbon sequestration benefits, and feedstocks with broad geographical diversity, expected to be widely available at a cost per unit energy (e.g. $/GJ) equal to that provided by oil were it is available at about $17/barrel.

The primary obstacle impeding the more widespread production of energy from biomass feedstocks is the general absence of low-cost technology for overcoming the recalcitrance of these materials. As outlined above, cellulosic ethanol can be produced from a wide variety of cellulosic biomass feedstocks including agricultural plant wastes (corn stover, cereal straws, sugarcane and sugarcane bagasse), plant wastes from industrial processes (sawdust, paper pulp), consumer waste and energy crops grown specifically for fuel production, such as switchgrass. Cellulosic biomass is composed of cellulose, hemicellulose and lignin, with smaller amounts of proteins, lipids (fats, waxes and oils) and ash. Roughly, two-thirds of the dry mass of cellulosic materials are present as cellulose and hemicellulose. Lignin makes up the bulk of the remaining dry mass.

The production of ethanol from biomass typically involves the breakdown or hydrolysis of lignocellulose-containing materials into disaccharides and, ultimately, monosaccharides. Biological processing cellulosic biomass aims to extract fermentable sugars from the feedstock. The sugars in cellulose and hemicellulose are locked in complex carbohydrates called polysaccharides (long chains of monosaccharides or simple sugars). Separating these complex polymeric structures into fermentable sugars is essential to the efficient and economic production of cellulosic ethanol.

A number of processing options are employed to produce fermentable sugars from cellulosic biomass. One approach utilizes acid hydrolysis to break down the complex carbohydrates into simple sugars. An alternative method, enzymatic hydrolysis, utilizes pretreatment processes to first reduce the size of the material to make it more accessible to hydrolysis. Once pretreated, enzymes are employed to convert the cellulosic biomass to fermentable sugars, which can be fermented by industrial microorganisms to produce fuel ethanol or other useful chemicals, but it is critical to use an efficient process to keep costs as low as possible.

However, cellulosic ethanol production presents a number of challenges that must be met in order to economically and efficiently produce ethanol from biomass. For example, challenges exist in the removal of solids from the production stream of cellulosic ethanol. In the biological production of alcohol from plant materials, the biomass is mixed with hot water to produce a wort, which is fermented by a microorganism. The fermented contents are then typically discharged as a slurry ("beer") and then alcohol is removed by distillation. The remainder, after distillation, is non-fermented insoluble material known as "stillage," and consists of a large amount of water together with the solids. Another challenge is the recalcitrance of lignocellulosic material to breakdown and the high cost of enzymes used in this conversion.

Many factors are involved in efficient bioprocessing, but the final concentration of product and good mixing are two of the most important. In order to achieve a high concentration of the fuel or chemical product, it is necessary to start with high concentrations of an initial starting material (substrate). With biomass fermentation, the use of high substrate concentrations creates problems for another key factor, mixing. Cellulosic biomass is highly fibrous, strong and water-absorbing, making it very difficult to mix at high concentrations. Mechanical mixing of cellulosic biomass requires a great deal of energy expense in the form of electricity to drive the impellers and is costly.

It would therefore be an advance in the art to achieve good mixing with less need for mechanical agitation so that high substrate concentrations can be used. The present invention describes a new way to achieve good mixing in biomass fermentation, without costly mechanical agitation of the biomass substrate, by using a flow-through reactor.

BRIEF SUMMARY OF THE INVENTION

The present invention provides a process for biomass fermentation without physical agitation of the biomass substrate. The present invention uses a flow-through reactor such as a percolation reactor containing pretreated biomass for fermenting the biomass to produce ethanol or other useful chemical products.

In the present invention, the recirculation of fermentation liquids limits the need for mechanical agitation of the biomass substrate and is expected to provide a cost savings of approximately 5% of the operating cost to produce ethanol.

In a first process of the present invention, for biologically converting carbohydrates from lignocellulosic biomass, a biomass substrate is suspended in a flow-through reactor; reaction liquids are absorbed into the biomass substrate and allowed to migrate through the biomass substrate into a liquid reservoir. In certain embodiments, the process can optionally include pre-treating a lignocellulosic feedstock to produce a pretreated biomass substrate. The portion of the reaction solution in the liquid reservoir may optionally be mixed or stirred. The reaction solution in the liquid reservoir is recirculated at least once to pass through the biomass substrate and percolate into the liquid reservoir again. The pretreated biomass substrate is thereby converted to sugars which are thereafter fermented to produce ethanol. The reaction solution can be further removed from the reactor and processed to separate the ethanol from non-fermented solids.

In certain embodiments of the process of the present invention, pre-treating is selected from the group consisting of catalytic treatment, acid treatment, alkaline treatment, organic solvent treatment, steam treatment, heat treatment, low-pH treatment, pressure treatment, milling treatment, steam explosion treatment, pulping treatment or white rot fungi treatment and combinations thereof. In further embodiments, the pre-treatment is a combination of steam treatment and heat treatment or steam and acid treatment.

In certain embodiments of the process, converting carbohydrates from the pretreated lignocellulosic biomass in a flow-through reactor comprises hydrolyzing cellulose, hemicellulose, or combinations thereof to form oligosaccharides, monomeric sugars, or a combination thereof, and fermenting said oligosaccharides, monomeric sugars, or a combination thereof to produce ethanol.

In some further embodiments of the present invention, hydrolyzing comprises enzymatically hydrolyzing cellulose and hemi-cellulose to form monomeric sugars. In certain embodiments, said hydrolyzing comprises chemically hydrolyzing cellulose and hemi-cellulose to form monomeric sugars.

In certain embodiments, said hydrolyzing and fermenting occur concurrently in the same reactor and in certain embodiments of the present invention hydrolyzing and fermenting are separate. The hydrolyzing and fermenting can occur in the presence of activated carbon in free or sequestered form and in some further embodiments, said activated carbon is granulated or powdered. In certain embodiments, the activated carbon can be added to the biomass substrate and in other embodiments it may be added to the liquid reservoir of the reactor vessel.

In some further embodiments of the present invention, the flow through reactor may be used for the liquefaction of biomass. As the cellulose and hemicellulose in the biomass substrate is broken down, the substrate material becomes more and more liquid and amendable to a traditional bioreactor.

Further embodiments, features, and advantages of the present invention, as well as the structure and operation of the various embodiments of the present invention, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS/FIGURES

The accompanying figures, which are incorporated herein and form part of the specification, illustrate a process for biologically converting carbohydrates, such as cellulose and hemicellulose, from lignocellulosic biomass without physical agitation of the biomass substrate. Together with the description, the figures further serve to explain the principles of a process for biologically converting, carbohydrates from lignocellulosic biomass in a flow-through reactor described herein and thereby enable a person skilled in the pertinent art to make and use a process of biologically converting biomass in a flow-through reactor.

DETAILED DESCRIPTION OF THE INVENTION

Figure 1:
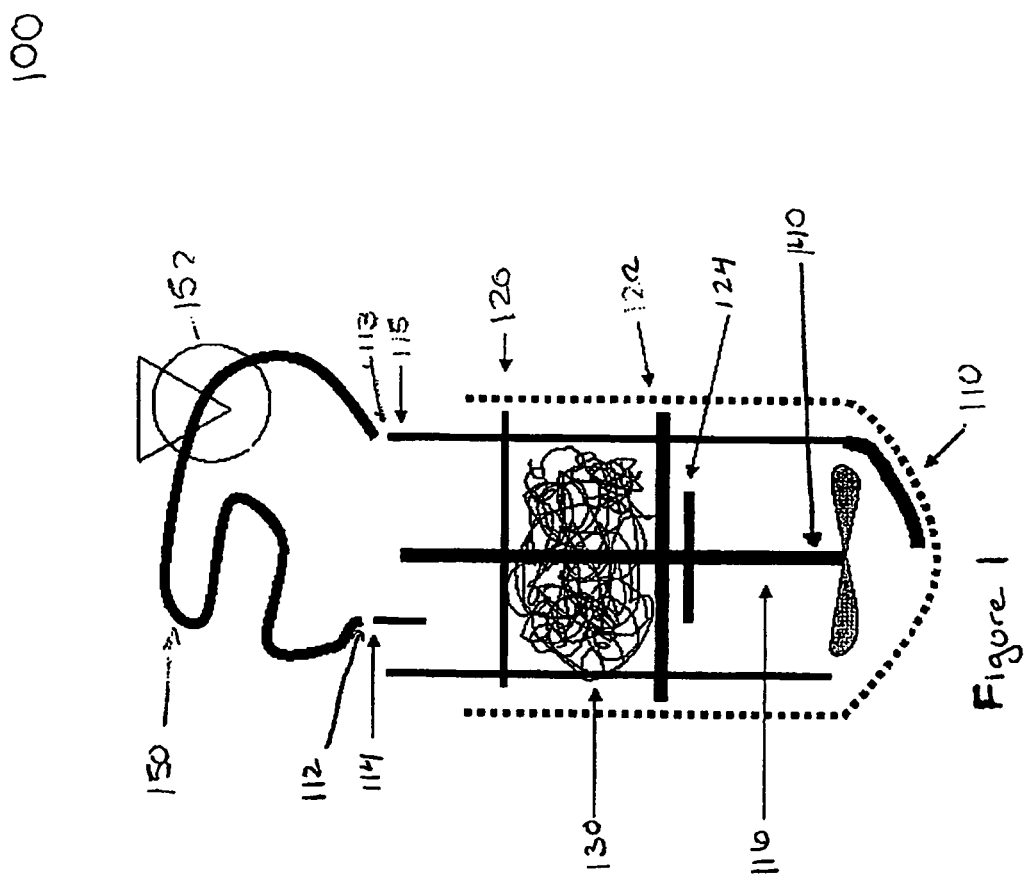
FIG. 1 is a schematic view of a flow-through reactor that can be used in a process for fermenting lignocellulosic biomass in accordance with present invention.

Reference will now be made in detail to embodiments of the present invention with reference to the accompanying figures, in which like reference numerals indicate like elements.

In one aspect, the present invention provides a process for biologically converting carbohydrates, such as cellulose and hemicellulose, from lignocellulosic biomass without physical agitation of the biomass substrate. The present invention uses a flow-through reactor such as a percolation reactor containing biomass for biologically converting the biomass substrate.

In the present invention, the recirculation of reaction liquids limits the need for mechanical agitation of the biomass substrate and is expected in certain instances to provide a cost savings of approximately 5% of the operating cost to produce ethanol. Additionally, higher substrate concentrations can be utilized because mechanical cr physical agitation of the biomass substrate is not necessary.

In certain embodiments, the process of biologically converting carbohydrates from lignocellulosic biomass can include fermenting the biomass substrate to produce ethanol.

In some further embodiments, other useful chemicals can be produced from the biological conversion of the biomass substrate. For example, the biomass may be converted to furfurals, acetone, ketones, butenes, ethers, ethylenes, esters, organic acids, or combinations thereof.

The present invention is directed to a process of biologically converting carbohydrates from lignocellulosic biomass in a flow-through reactor, which comprises: suspending a biomass substrate in a flow-through reactor; passing reaction liquids into the reactor and allowing the liquids to be absorbed into the biomass substrate and a portion of the reaction solution migrates through the biomass substrate into a liquid reservoir; and recirculating the reaction liquids in the liquid reservoir at least once. In certain embodiments, the biological conversion can include fermenting the biomass substrate to produce ethanol.

Biomass is material made by the growth of living organisms. Cellulose-containing plants and waste products are the most abundant forms of biomass, such materials are referred to as lignocellulosic biomass because they contain cellulose (20% to 60%), hemicellulose (10% to 40%) and lignin (5% to 25%) whilst non-woody biomass generally contains less than about 15-20% lignin.

The term "hemicellulose," "hemicellulosic portions," and "hemicellulosic fractions" mean the non-lignin, non-cellulose elements of lignocellulosic material, such as but not limited to hemicellulose (comprising xyloglucan, xylan, glucuronoxylan, arabinoxylan, mannan, glucomannan, and galactoglucomannan, inter alia), pectins (e.g., homogalacturonans, rhamnogalacturonan I and II, and xylogalacturonan), and proteoglycans (e.g., arabinogalactan-protein, extensin, and proline-rich proteins).

In certain embodiments lignocellulosic biomass can include, but is not limited to, woody biomass, such as recycled wood pulp fiber, sawdust, hardwood, softwood, and combinations thereof; grasses, such as switch grass, cord grass, rye grass, reed canary grass, miscanthus, mixed prairie grasses, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, beet pulp, palm residue, and corn fiber; stover, such as but not limited to soybean stover, corn stover; and forestry wastes, such as but not limited to recycled wood pulp fiber, sawdust, hardwood (e.g., poplar, oak, maple, birch), softwood, or any combination thereof.

Paper sludge is also a viable feedstock for ethanol production. Paper sludge is solid residue arising from pulping and paper-making, and is typically removed from process wastewater in a primary clarifier. The size range of the substrate material varies widely and depends upon the type of substrate material used as well as the requirements and needs of a given process. In certain embodiments of the invention, the lignocellulosic biomass may be prepared in such a way as to permit ease of handling in conveyors, hoppers and the like. In the case of wood, the chips obtained from commercial chippers are suitable; in the case of straw it is sometimes desirable to chop the stalks into uniform pieces about 1 to about 3 inches in length. Depending on the intended degree of pretreatment, the size of the substrate particles prior to pretreatment may range from less than a millimeter to inches in length.

Cellulose molecules are linear, unbranched and can have polymerization ranges from 500 to 20,000 and have a strong tendency to form inter- and intra-molecular hydrogen bonds. Bundles of cellulose molecules are thus aggregated together to form microfibrils in which highly ordered (crystalline) regions alternate with less ordered (amorphous) regions. Microfibrils make fibrils and finally cellulose fibers. As a consequence of its fibrous structure and strong hydrogen bonds, cellulose has a very high tensile strength and is insoluble in most solvents.

Lignocellulosic biomass must therefore undergo pre-treatment to enhance susceptibility to hydrolysis. The degradation of lignocellulosics is primarily governed by its structural features because cellulose possesses a highly ordered structure and the lignin surrounding cellulose forms a physical barrier.

Pretreatment is required to reduce the lignin content, reduce the order of the cellulose and increases surface area. Pretreatment methods can be physical, chemical, physicochemical and biological, depending on the mode of action. The various pretreatment methods that have been used to increase cellulose digestibility include ball-milling treatment, two-roll milling treatment, hammer milling treatment, colloid milling treatment, high pressure treatment, radiation treatment, pyrolysis, catalytic treatment, acid treatment, alkaline treatment, organic solvent treatment, steam treatment, heat treatment, low-pH treatment, steam explosion treatment, pulping treatment, white rot fungi treatment, steam explosion and ammonia fiber explosion and combinations thereof. A further discussion of pretreatments can be found in Holtzapple et al. (U.S. Pat. No. 5,865,898; hereby incorporated by reference). Exposure time, temperature, and pH are the additional metrics that govern the extent to which the cellulosic carbohydrate fractions cleaved during pre-treatment are amenable to further enzymatic hydrolysis in subsequent biological conversion steps.

The resultant carbohydrate mixture (referred to as biomass substrate herein) produced from pre-treatment methods can be further converted to monosaccharides using acid hydrolysis, enzyme hydrolysis or microbes. If acid hydrolysis is used, the process will require a neutralization step before fermentation. For example, the fluid intake of the reactor is modified to allow for the addition of acid into the reactor for converting the biomass by acid hydrolysis. Next, the reaction solution in the reactor is neutralized by adding neutralizing agents into the fluid intake before further converting the biomass through a fermentation step. Microbial hydrolysis produces cellular biomass (single-cell protein) and metabolic waste products, such as organic acids, whilst acid hydrolysis, although simple, produces many additional degradation products, however enzymatic hydrolysis by such enzymes as cellulases, endoglucanases, exoglucanases, cellobiohydrolases, β-glucosidases, xylanases, endoxylanases, exoxylanases, β-xylosidases, arabinoxylanases, mannases, galactases, pectinases, glucuronidases, amylases, α-amylases, β-amylases, glucoamylases, α-glucosidases, isoamylases provide the currently preferred approach. Such saccharification enzymes which perform hydrolysis may be produced synthetically, semi-synthetically, or biologically including using recombinant microorganisms.

In certain embodiments of the present invention fermentation organisms can be selected from bacteria, fungi, yeast or a combination thereof. In certain embodiments, useful organisms for biological conversion can include *Escherichia, Zymomonas, Saccharomyces, Candida, Pichia, Streptomyces, Bacillus, Lactobacillus,* and *Clostridium*. For example, a recombinant organism selected from the group consisting of *Escherichia coli, Zymomonas mobilis, Bacillus stearothermophilus, Saccharomyces cerevisiae, Clostridia thermocellum, Thermoanaerobacterium saccharolyticum, Pichia stipitis,* can be added to the reaction solution. In certain embodiments the recombinant organism may perform hydrolysis and fermentation concurrently.

"Fermentation" or "fermentation process" refers to any process comprising a fermentation step. A fermentation process of the invention includes, without limitation, fermentation processes used to produce alcohols, organic acids, ketones, amino acids, gases, antibiotics, enzymes, vitamins and hormones. Fermentation processes also include fermentation processes used in the consumable alcohol industry, dairy industry, leather industry and tobacco industry. The product of the fermentation process is referred to herein as beer.

In certain embodiments the biomass substrate is further converted to a beer, which contains ethanol and non-fermented solids, which are both recovered. Therefore, certain embodiments include biologically converting said biomass substrate to form a beer. In certain embodiments biologically converting the biomass substrate to form a beer comprises the addition of bacteria, fungi, yeast or a combination thereof.

In certain embodiments the bacteria, or yeast can be selected from *Saccharomyces cerevisiae, Saccharomyces carlsbergensis, Brettanomyces* sp., *Saccharomyces pastorianus., Pichia* spp., *Thermoanaerobacter* sp., *Thermoanaerobacterium* sp., *Clostridium* sp., *Zymomonas* sp., and combinations thereof.

In one embodiment, the process is conducted in a flow-through reactor that is a single reactor vessel, as shown in FIG. 1. Flow-through reactor 100 includes a reactor vessel 110, fluid intake passageway 114, fluid outtake passageway 115 and fluid passageway 150.

Reactor vessel 110 contains a liquid reservoir 116, a first perforated screen or disc 120, a second perforated screen or disc 122, a fluid intake passageway 114, and fluid outtake passageway 115.

Within reactor vessel 110, first perforated screen 120 and second perforated screen 122 are suspended spaced apart to allow for a biomass substrate 130 to be suspended between first perforated screen 120 and second perforated screen 122. Second perforated screen 122 is supported by support member 124. Support member 124 may be a metal disc or spoked ring or any other suitable support member known to one of ordinary skill in the art. First perforated screen 120 distributes liquids flowing through reactor 100 evenly and allows liquids to flow through screen 120 and be absorbed into biomass substrate 130. Second perforated screen 122 is below biomass substrate 130 and allows a reaction solution to migrate through to liquid reservoir 116.

Perforated screens 120 and 122 can be perforated discs or screens, mesh screens, a membrane or any other suitable straining screen that will allow liquids to percolate through and be absorbed by the biomass substrate, and migrate through to the liquid reservoir. This arrangement allows for liquids and the biomass substrate to mix because of gravity and reduces the need for physical or mechanical agitation of biomass substrate 130. Optionally, migration of the reaction solution can be driven by pressure.

As shown in FIG. 1, a portion of the reaction solution migrates through biomass substrate 130 into liquid reservoir 116 below perforated screens 120 and 122. The liquid reservoir is provided for collecting the reaction solution/liquids for recirculation or further processing. Additionally, the reaction solution can be optionally mixed in liquid reservoir 116. If the reaction solution is mixed, it should be stirred at a rate of about 60 rpm to about 200 rpm.

The reaction solution contains nutrients for converting carbohydrates from the biomass substrate. The reaction solution nutrients may include a microorganism and cellulase enzymes. In certain embodiments, a cellulolytic organism may be used and cellulase enzymes may optionally be omitted.

If the reaction solution is mixed or stirred, a mixing device 140 can be provided. In certain embodiments, mixing device 140 may be an impeller for stirring the reaction solution. The impeller may be a disc-type impeller, a boat-type impeller, or any other suitable mixing device that allows for stirring of the reaction solution. Also, the mixing device 140 can be a single impeller, a double impeller, or any number of impellers.

Also, liquid outtake passageway 115 is disposed in reactor vessel 110 to allow for the reaction liquids to be removed from liquid reservoir 116 and recirculated. One end of liquid outtake passage way 115 is disposed in liquid reservoir 116 and another end is connected to fluid passageway 150 at outlet port 113 in reactor vessel 110.

Fluid passageway 150 is connected to reactor vessel 110 at outlet port 113 and an inlet port 112 for recirculating the reaction solution, meaning that liquids can be removed from reactor vessel 110 and then fed back into reactor vessel 110 to be absorbed and percolated through biomass substrate 130 again. The reaction solution can be drawn out of reactor vessel 110 through outtake passageway 115, into passageway 150 and then returned via fluid intake passageway 114 to be redistributed and absorbed into biomass substrate 130.

By recirculating the reaction solution, good mixing of the liquids with the biomass substrate can be achieved without having to physically agitate biomass substrate 130. This is expected to reduce operating costs by approximately 5%.

Additionally, a higher concentration of the initial biomass substrate can be used. Typically, a maximum of 20-25% solids is the initial concentration of the biomass substrate that can be used in a fermentation process. In certain embodiments of the present invention, the flow-through reactor with recirculation of the reaction liquids allows for initial concentrations of the biomass substrate up to 30-40% solids. The higher initial concentration of the biomass substrate enables higher concentrates of ethanol to be produced. For example, with compression of the biomass substrate, 35% solids can be used will still having some free reaction solution migrating through the substrate.

As shown in FIG. 1, recirculation of the reaction solution can be facilitated by a pump 152 disposed within passageway 150. Pump 152 assists by drawing the reaction solution into liquid outtake passageway 115 and fluid passageway 150. In other embodiments, pump 152 may not be provided and recirculation may be driven by the build-up of fermentation gases, such as $CO_2$, in reactor vessel 110. The build-up of fermentation gases increases the pressure in reactor vessel 110 and forces the reaction solution into outtake passageway 115 and fluid passageway 150.

Additionally, reactor 100 can be provided with a heating mechanism for heating the reaction liquids and biomass substrate 130. In certain embodiments, an electrical heating jacket can be fitted around reactor vessel 110 for heating the reaction liquids and the pretreated biomass substrate to facilitate fermentation. In other embodiments, a heating mechanism can be placed within fluid passageway 150 to directly heat the reaction liquids.

The reaction solution should be heated to a temperature between about 20° C. to about 60° C. depending on the nutrients in the reaction solution. For example, if the reaction solution contains a mesophilic organism such as *Saccharomyces cerevisiae* or *Escherichia coli*, the temperature should range from about 30° C. to about 42° C. If a thermophilic organism such as *Thermoanaerobacterium saccharolyticum* is used, the reaction solution should be heated to a temperature between about 50° C. to about 60° C.

Additionally, the pH of the reaction solution should between about 4.0 and about 8.0. The appropriate pH range of the reaction solution will also depend on the nutrients in the reaction solution. For example, if *Thermoanaerobacterium saccharolyticum* is used the pH range for the reaction solution should be between about 5.0 and about 6.5.

In one embodiment of the present invention, the process comprises suspending biomass 130 within reactor vessel 110 between perforated discs 120 and 122. Biomass substrate 130 is highly absorbent. To ensure that some reaction solution is free to percolate/migrate through biomass substrate 130, biomass substrate 130 can be compressed. Biomass substrate 130 may be compressed into a cake before suspending in reactor vessel 110 to achieve a higher initial concentration of solids while still maintaining an appropriate volume of free reaction solution. The amount of free reaction solution should be from about 5% to about 40% of the total volume of liquids. Alternatively, biomass substrate 130 may be suspended in reactor vessel 110 and then compressed between perforated discs 120 and 122.

In certain embodiments of the present invention, the lignocellulosic biomass substrate is selected from the group consisting of grass, switch grass, cord grass, rye grass, reed canary grass, miscanthus, mixed prairie grasses, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

Once the biomass substrate 130 is suspended in reactor 110, a reaction solution is then passed over perforated disc 120 and evenly distributed for absorption into biomass substrate 130 and migrates through the substrate into liquid reservoir 116 below. The migration of the free reaction solution may be driven by gravity. In other embodiments the migration may be pressure driven.

Depending on the height at which biomass substrate 130 is suspended and the volume of reaction solution used, part of biomass substrate 130 may be submerged in the reaction solution in liquid reservoir 116. Passing the reaction solution through biomass substrate 130 allows for digestion of biomass substrate 130 and fermentation.

In certain embodiments of the present invention the reaction solution can comprise fermentation organisms and cellulase enzymes. The fermentation organism can be selected from bacteria, fungi, yeast or a combination thereof. In certain embodiments the bacteria, or yeast can be selected from *Saccharomyces cerevisiae, Saccharomyces carlsbergensis, Brettanomyces* sp., *Saccharomyces pastorianus., Pichia* spp., *Thermoanaerobacter* sp., *Thermoanaerobacterium* sp., *Clostridium* sp., *Zymomonas* sp., and combinations thereof. If a cellulolytic organism is used in the reaction solution, then cellulase enzymes can be omitted from the reaction liquids.

Once at least a portion of the reaction solution flows through to liquid reservoir 116, the portion in the liquid reservoir (i.e. free reaction solution) is recirculated at least once, meaning that the reaction liquids are removed from the liquid reservoir 116 through fluid outtake line 115, flow through fluid passageway 150 and are fed back into reactor vessel 110 migrate through the biomass substrate again. The flow rate is adjusted to provide useful contact times of the reaction solution with the biomass substrate. For instance, a useful flow rate of the reaction solution migrating through substrate 130 should be between about 0.5% to about 10% of the total volume per minute.

The recirculation of the reaction liquids can be facilitated by a pump 152 in fluid passageway 150 that draws the liquids into fluid outtake line 115. Alternatively, the recirculation of the reaction liquids can be driven by the build up of gases in the reactor vessel. Recirculation of the reaction solution reduces/eliminates the need to mechanically or physically agitate biomass substrate 130 with the reaction liquids.

Recirculation of the reaction solution can be continuous or intermittent during the degradation and fermentation of pretreated biomass substrate 130. The hydrolysis and fermentation processes should last for about 24 to about 160 hours. As biomass substrate 130 degrades over time and during the recirculation, the reaction solution will turn into a beer as the fermentation process progresses and may contain non-fermented insoluble material ethanol, as well as other useful chemical products.

In certain embodiments, reactor 100 may be provided with a filter to prevent the insoluble material from clogging fluid outtake passageway 115, fluid passageway 150 and fluid intake passageway 114. A filter may be disposed in any number of locations such as, for example, fluid outtake passageway 115, outlet port 113, fluid passageway 150, inlet port 112 or intake passageway 114. In other embodiments, a plurality of filters may be used to prevent the clogging of fluid outtake 115, fluid passageway 150 and fluid intake 114.

Once biomass substrate 130 is substantially degraded and fermented, the process of the present invention may further comprise removing the beer in batch-mode from reactor 100 and processing the beer to remove the ethanol. The beer may be distilled to separate the ethanol from the non-fermented insoluble material.

In certain embodiments, the process can further include hydrolyzing the lignocellulosic biomass in the flow-through reactor. Hydrolyzing the biomass may comprise enzymatically or chemically hydrolyzing cellulose and hemi-cellulose in biomass substrate 130 to form monomeric sugars. The monomeric sugars than may be fermented to produce ethanol.

In certain embodiments of the present invention, hydrolyzing and fermenting are concurrent and may occur in the presence of activated carbon in free form and in some further embodiments, the activated carbon is granulated or powdered. The activated carbon may be added to the liquids in the reactor. In other embodiments, the activated carbon in free form can be directly added to the lignocellulosic biomass substrate suspended in the flow-through reactor.

In some other embodiments of the present invention, the flow-through reactor may be used for the liquefaction of biomass. As the cellulose and hemicellulose in the biomass substrate is broken down, the substrate material becomes more and more liquid and amendable to a traditional bioreactor. At a certain point, the reaction solution may be transferred to a traditional bioreactor for further processing. Alternatively, the flow through reactor may be set up within a bioreactor. In this embodiment, as the biomass substrate is liquefied, it will drip through perforated disc 122 into reservoir 116 and then may be fed into a bioreactor for additional processing.

Figure 2:
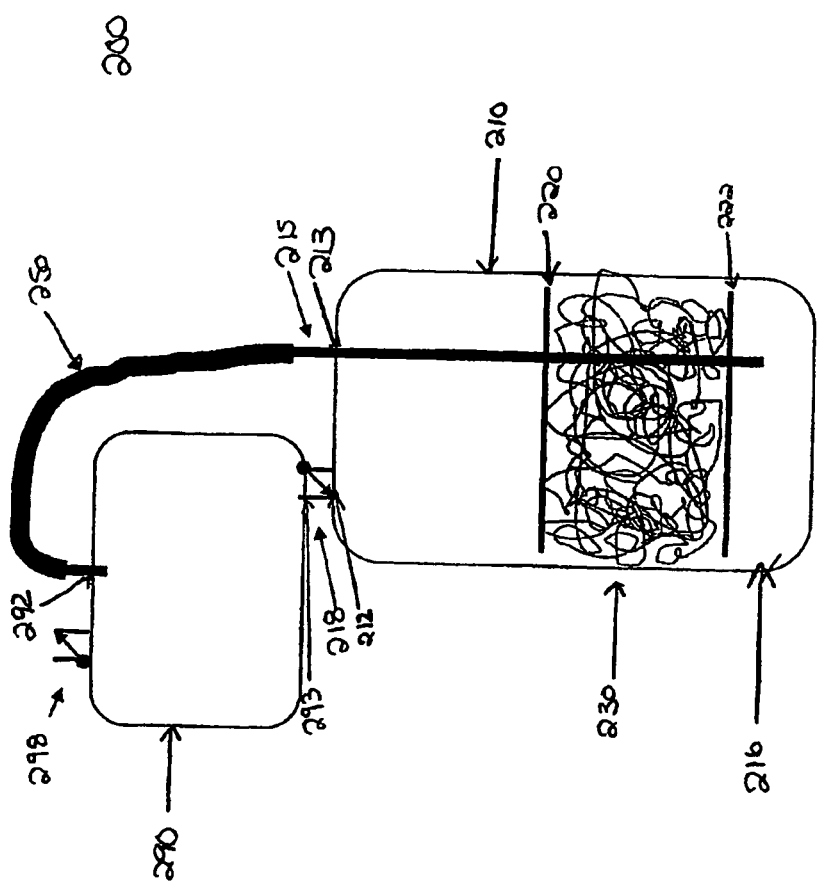
FIG. 2 is a schematic view of another flow-through reactor that can be used in a process for fermenting lignocellulosic biomass in accordance with present invention.

In another embodiment, the process can be performed in a flow-through reactor as shown in FIG. 2. In this embodiment, recirculation of the reaction liquids is driven by the build-up of gases in reactor vessel 210 due to fermentation of biomass substrate 230.

Flow-through reactor 200 includes a reactor vessel 210 and a reservoir tank 290. Reactor vessel 210 includes an inlet port 212, an outlet port 213, a liquid reservoir 216, and a fluid outtake passageway 215. Within inlet port 212, a one-way check valve 218 is disposed, which fluidly connects reactor vessel 210 and reservoir tank 290. Liquids can flow from tank 290 through outlet 293 and into vessel 210 at inlet port 212, but gas cannot flow through port 212 into tank 290.

Within reactor vessel 210, a first perforated screen or disc 220 and a second perforated screen disc 222 are contained for suspending biomass 230 within vessel 210. Below second perforated screen 222 is liquid reservoir 216. One end of fluid outtake passageway 215 is disposed within liquid reservoir 216 and another end, extends out of vessel 210 through outlet port 213, to fluidly connect with fluid passageway 250. Passageway 250 is connected to reservoir tank 290 at inlet 292.

In this embodiment, the process involves suspending pretreated biomass substrate 230 between first perforated screen 220 and second perforated screen 222.

Initially a reaction solution is contained only in reactor vessel 210. Reservoir tank 290 is empty and vented to the outside atmosphere through one-way check valve 298.

Depending on the height at which pretreated biomass substrate 230 is suspended and the volume of reaction liquids used, part of pretreated biomass substrate 230 may be submerged in the reaction solution.

The reaction solution passes through pretreated biomass substrate 230 to digest and ferment biomass substrate 230. Pressure from fermentation of the biomass substrate builds within reactor vessel 210 and forces a portion of the free reaction solution up into outtake passageway 215, through passageway 250 and into reservoir tank 290 where the reaction liquids collect.

When the level of the reaction solution in reactor vessel 210 drops below the bottom of outtake passageway 215, gases within vessel 210 will be forced up into outtake passageway 215, through fluid passageway 250, into reservoir tank 290, where the gases are vented to the outside atmosphere through check valve 298.

As such, pressure in reactor 210 and reservoir tank 290 will equalize, and the reaction solution in reservoir tank 290 will flow through outlet port 293 through one-way check valve 218 into the top of reactor 210. Then the recirculated reaction liquids will percolate down through perforated screen 220 and biomass substrate 230 and a portion will migrate through perforated screen 222.

As the level of reaction solution in reactor 210 raises in reservoir 216, eventually the liquid level will reach the bottom of outtake passageway 215 and start the recirculation of the reaction solution again.

In other embodiments, recirculation may be further facilitated through use of a pumping mechanism. For example, a pump may be disposed within passageway 250 to assist by drawing the reaction liquids into liquid outtake passageway 215 and fluid passageway 250.

EXAMPLES

The following experiment was performed in an apparatus as shown in FIG. 1.

TABLE 1

A Simultaneous Saccarification Fermentation (SSF) process

| | |
|---|---|
| 1 | Add to reactor vessel:<br>664 ml $H_2O$<br>5 g activated carbon<br>1 ml resazurin<br>30 ml $NH_4OH$ |
| 2 | Suspend in reactor vessel:<br>175 g MS028 (pretreated hardwood substrate) |
| 3 | Autoclave reactor vessel for 40 min |
| 4 | Add to reactor vessel:<br>180 ml of filter-sterilized concentrated bacterial growth medium |
| 5 | Purge with filter $N_2$ for 1 hour |
| 6 | Set temperature @ 55° C., stirring @ 150 rpm |
| 7 | Add:<br>27 ml Spezyme CP (cellulase- breaks down oligosaccharides) |
| 8 | Inoculate and ferment, temp 55, pH 5.5, rpm 150 |

The experiment showed proof of concept that ethanol can be produced from biomass in accordance with the process of the invention.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A process for biologically converting carbohydrates from lignocellulosic biomass, comprising the steps of:
   suspending lignocellulosic biomass in a flow-through reactor, wherein said reactor comprises:
      a reactor vessel having a fluid inlet and a fluid outlet;
      a reservoir tank having a fluid inlet and a fluid outlet, wherein said fluid outlet of said reservoir tank is fluidly connected to said fluid inlet of said reactor vessel; and
      a fluid passageway, wherein one end of said passageway is connected to said fluid outlet of said reactor vessel and another end of said passageway is connected to said fluid inlet of said reservoir tank;
   passing a reaction solution into said reactor, wherein said reaction solution is absorbed into said biomass and at least a portion of said reaction solution migrates through said biomass substrate to a liquid reservoir in said reactor vessel; and
   recirculating said reaction solution in said liquid reservoir at least once, wherein said reaction solution flows from said fluid outlet of said reactor vessel through said passageway to said reservoir tank and then into said fluid inlet of said reactor vessel;
   whereby a portion of carbohydrates in said lignocellulosic biomass are biologically converted,
   wherein said biological conversion comprises fermenting oligosaccharides, monomeric sugars, or a combination thereof to produce a fermentation product,
   and wherein said recirculation of said solution is driven by a build-up of fermentation gases in said flow-through reactor.

2. The process for biologically converting carbohydrates from lignocellulosic biomass according to claim 1, wherein said lignocellulosic biomass is pretreated before suspending in said reactor.

3. The process for biologically converting carbohydrates from lignocellulosic biomass according to claim 1, wherein said migration of said reaction solution is driven by gravity.

4. The process for biologically converting carbohydrates from lignocellulosic biomass according to claim 1, wherein said migration of said reaction solution is driven by pressure.

5. The process for biologically converting carbohydrates from lignocellulosic biomass according to claim 1, wherein a portion of said carbohydrates is biologically converted by:
   (a) hydrolyzing cellulose, hemicellulose, or a combination thereof to form oligosaccharides, monomeric sugars, or a combination thereof;
   (b) fermenting oligosaccharides, monomeric sugars, or a combination thereof to produce ethanol; or
   (c) a combination thereof.

6. The process for biologically converting carbohydrates from lignocellulosic biomass according to claim 5, wherein a portion of said carbohydrates is biologically converted by fermenting oligosaccharides, monomeric sugars, or a combination thereof to produce ethanol and further comprising:
   removing said reaction solution in said liquid reservoir; and
   processing said solution to separate ethanol and non-fermented solids in said reaction solution.

7. The process for biologically converting carbohydrates from lignocellulosic biomass according to claim 6, wherein the processing said solution to separate ethanol and non-fermented solids is selected from the group consisting of beer column tray separation, paddle dryer apparatus separation, twin screw conveyer separation, rotary valve separation, butterfly valve separation, distillation, centrifuging and combinations thereof.

8. The process for biologically converting carbohydrates from lignocellulosic biomass according to claim 1, wherein said biomass substrate is at least partially submerged in said reaction solution in said liquid reservoir.

9. The process for biologically converting carbohydrates from lignocellulosic biomass according to claim 1, wherein said lignocellulosic biomass is selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, beet pulp, palm residue, corn fiber, stover, soybean stover, corn stover, forestry wastes, recycled wood pulp fiber, paper sludge, sawdust, hardwood, softwood, and combinations thereof.

10. The process for biologically converting carbohydrates from lignocellulosic biomass according to claim 1, wherein the reaction solution includes fermentation organisms, cellulase enzymes, or a combination thereof.

11. The process for biologically converting carbohydrates from lignocellulosic biomass according to claim 1, wherein said reactor vessel comprises:
a first perforated screen and a second perforated screen, wherein said biomass is suspended between said first perforated screen and said second perforated screen.

12. The process for biologically converting carbohydrates from lignocellulosic biomass according to claim 11, wherein said flow-through reactor further comprises:
a pump to facilitate recirculating said reaction solution, wherein said pump is disposed in said fluid passageway.

13. The process for biologically converting carbohydrates from lignocellulosic biomass according to claim 1, wherein activated carbon is added to said biomass or said liquid reservoir.

14. The process for biologically converting carbohydrates from lignocellulosic biomass according to claim 1, wherein:
said fermentation product is ethanol;
said reactor vessel contains a first perforated screen and a second perforated disc; and
said reservoir tank contains a one-way check valve.

15. A process for producing ethanol from lignocellulosic biomass, comprising the steps of:
suspending pretreated lignocellulosic biomass in a flow-through reactor;
hydrolyzing said biomass to form monomeric sugars;
passing a reaction solution through said biomass; wherein said reaction solution is absorbed into said biomass and at least a portion of said solution migrates through said biomass substrate to a liquid reservoir;
recirculating said reaction solution in said liquid reservoir at least once; and
fermenting said monomeric sugars to produce ethanol, wherein said recirculation of said solution is driven by a build-up of fermentation gases in said flow-through reactor.

16. The process for producing ethanol according to claim 15, further comprising:
removing said reaction solution in said liquid reservoir; and
processing to separate ethanol and non-fermented solids in said reaction solution.

17. The process of claim 15, wherein said hydrolyzing comprises enzymatically hydrolyzing cellulose and hemi-cellulose to form monomeric sugars.

18. The process of claim 15, wherein said hydrolyzing comprises chemically hydrolyzing cellulose and hemi-cellulose to form monomeric sugars.

19. The process of claim 15, wherein said fermenting comprises enzymatically fermenting said monomeric sugars to produce ethanol.

20. The process of claim 15, wherein said hydrolyzing and fermenting occur concurrently.

21. The process of claim 20, wherein hydrolyzing and fermenting occur in the presence of activated carbon.

22. The process of claim 21, wherein said activated carbon is added to said liquid reservoir.

23. The process of claim 21, wherein said activated carbon is added to said biomass.

24. The process of claim 15, wherein said flow-through reactor comprises:
a reactor vessel having a fluid inlet and a fluid outlet; and
a fluid passageway, wherein one end of said passageway is connected to said fluid outlet of said reactor vessel and another end of said passageway is connected to said fluid inlet of said reactor vessel.

25. The process of claim 15, wherein said flow-through reactor comprises:
a reactor vessel having a fluid inlet and a fluid outlet;
a reservoir tank having a fluid inlet and a fluid outlet, wherein said fluid outlet of said reservoir tank is fluidly connected to said fluid inlet of said reactor vessel; and
a fluid passageway, wherein one end of said passageway is connected to said fluid outlet of said reactor vessel and another end of said passageway is connected to said fluid inlet of said reservoir tank.

26. The process of claim 15, wherein said migration of said reaction solution is driven by gravity.

27. The process of claim 15, wherein said migration of said reaction solution is driven by pressure.

* * * * *